(12) United States Patent
Sweitzer

(10) Patent No.: US 11,440,177 B2
(45) Date of Patent: Sep. 13, 2022

(54) HANDLE ASSEMBLY FOR A SURGICAL TOOL

(71) Applicant: Shukla Medical, St. Petersburg, FL (US)

(72) Inventor: Zachary Robert Sweitzer, Keyport, NJ (US)

(73) Assignee: Shukla Medical, St. Petersburg, FL (US)

( * ) Notice: Subject to any disclaimer, the term of this patent is extended or adjusted under 35 U.S.C. 154(b) by 0 days.

(21) Appl. No.: 16/834,230

(22) Filed: Mar. 30, 2020

(65) Prior Publication Data

US 2021/0298917 A1   Sep. 30, 2021

(51) Int. Cl.

| | |
|---|---|
| *B25G 3/24* | (2006.01) |
| *B25G 3/12* | (2006.01) |
| *B25G 3/18* | (2006.01) |
| *B25G 3/20* | (2006.01) |
| *A61F 2/46* | (2006.01) |
| *B25G 1/04* | (2006.01) |
| *A61B 17/00* | (2006.01) |

(52) U.S. Cl.
CPC .................. *B25G 3/24* (2013.01); *A61F 2/46* (2013.01); *B25G 1/04* (2013.01); *B25G 3/12* (2013.01); *B25G 3/18* (2013.01); *B25G 3/20* (2013.01); *A61B 2017/0046* (2013.01)

(58) Field of Classification Search
CPC ... B25G 3/18; B25G 3/20; B25G 3/24; B25G 3/12; A61B 2017/0046; A61F 2/46; A61F 2/4601; A61F 2/4603
See application file for complete search history.

(56) References Cited

U.S. PATENT DOCUMENTS

| 1,269,413 | A | * | 6/1918 | Finnigan | ............. | B25B 23/0021 |
| | | | | | | 81/177.2 |
| 1,484,379 | A | * | 2/1924 | Rainey | .................... | B25G 1/00 |
| | | | | | | 81/177.1 |
| 4,442,601 | A | | 4/1984 | Hirsch et al. | | |

(Continued)

OTHER PUBLICATIONS

Pages 1 and 5 of an internal PowerPoint presentation entitled Shukla Shoulder System Universal Shoulder Extraction System, Preview Fall 2020.

(Continued)

*Primary Examiner* — Jeffrey O'Brien
(74) *Attorney, Agent, or Firm* — Kim IP Law Group LLC

(57) ABSTRACT

A handle assembly for a surgical tool including a handle having a distal end, and a first retaining mechanism attached to the distal end of the handle. The retaining mechanism includes a first retaining housing having a first central cavity for receiving a surgical tool, and a first locking mechanism moveable between first and second positions relative to the housing, the locking mechanism including a through hole for receiving the surgical tool. The handle assembly further includes a second retaining mechanism attached to a proximal end of the handle. The second retaining mechanism includes a second retaining housing having a second central cavity for receiving a handle extension, and a second locking mechanism moveable between first and second positions relative to the second retaining housing, the second locking mechanism having a through hole for receiving the handle extension.

16 Claims, 21 Drawing Sheets

(56) References Cited

U.S. PATENT DOCUMENTS

| | | | | |
|---|---|---|---|---|
| 5,931,065 | A * | 8/1999 | Jackson | B25B 23/0021 81/177.2 |
| 6,010,508 | A | 1/2000 | Bradley | |
| 6,170,161 | B1 * | 1/2001 | Stein | A47J 37/0786 30/160 |
| 6,266,885 | B1 * | 7/2001 | Stein | A47J 37/0786 30/160 |
| 6,374,500 | B2 * | 4/2002 | Stein | A47J 37/0786 30/160 |
| 7,467,575 | B2 * | 12/2008 | Lai | B25B 15/02 81/177.1 |
| 7,494,304 | B2 * | 2/2009 | McAuliffe | B23G 1/261 408/124 |
| 7,587,791 | B2 * | 9/2009 | Liou | B25B 23/0035 16/422 |
| 9,255,591 | B2 * | 2/2016 | Carnevali | F16B 1/00 |
| 9,498,879 | B1 * | 11/2016 | Morad | B25G 3/12 |
| 9,622,882 | B2 * | 4/2017 | Errico | A61F 2/0095 |
| 10,098,445 | B1 * | 10/2018 | Morad | A46B 5/0095 |
| 10,843,325 | B2 * | 11/2020 | Scheuber | A61B 17/162 |
| 10,959,738 | B2 * | 3/2021 | Sweitzer | A61B 17/1604 |
| 2007/0199412 | A1 * | 8/2007 | Lee | B25G 1/005 81/177.85 |
| 2010/0282035 | A1 * | 11/2010 | Wang | B25G 3/10 81/489 |
| 2011/0030225 | A1 * | 2/2011 | Wang | B44D 3/164 30/340 |
| 2014/0288566 | A1 * | 9/2014 | Green, II | A61B 17/92 606/99 |
| 2019/0201008 | A1 | 7/2019 | Sweitzer | |
| 2020/0214781 | A1 * | 7/2020 | Luo | B25B 23/0042 |
| 2020/0214853 | A1 * | 7/2020 | Sweitzer | A61F 2/4603 |
| 2020/0229857 | A1 * | 7/2020 | Sweitzer | A61B 17/92 |
| 2021/0038205 | A1 * | 2/2021 | Milella, Jr. | B25G 3/02 |
| 2021/0038206 | A1 * | 2/2021 | Milella, Jr. | B25G 3/00 |
| 2021/0039244 | A1 * | 2/2021 | Milella, Jr. | B25G 3/02 |
| 2021/0068851 | A1 * | 3/2021 | Sweitzer | A61B 17/1613 |
| 2021/0093468 | A1 * | 4/2021 | Sweitzer | A61F 2/4612 |

OTHER PUBLICATIONS 3 still shots from video entitled "Shoulder System Overview" presented at FIVE Labs of Tampa, Fl on Oct. 24, 2020 and Jun. 12, 2021.

Extended European Search Report for European Patent Application No. 21165667.3, dated Aug. 19, 2021.

* cited by examiner

HANDLE ASSEMBLY FOR A SURGICAL TOOL

The exemplary embodiments of present invention relate generally to a handle assembly for a surgical tool and, more specifically, to a handle assembly including a handle having a distal end for releasably receiving a surgical tool and a proximal end for releasably receiving a handle extension.

BACKGROUND OF THE DISCLOSURE

A surgical tool is typically connected to a handle that is used to manipulate the tool. The surgical tool is provided at a distal end of the handle and is commonly permanently or integrally attached to the handle. In other instances, the surgical tool is removably attached to the handle.

In either case, if the surgical tool is an extraction tool, e.g., one used to extract implants from bone or the like, the handle by itself may not be capable of enabling a user, e.g., a surgeon, to exert leverage suitable to extract an implant.

BRIEF SUMMARY OF THE DISCLOSURE

In accordance with an exemplary embodiment there is provided a handle assembly for a surgical tool comprising a handle having a distal end, and a first retaining mechanism attached to the distal end of the handle. The first retaining mechanism includes a first retaining housing having a first central cavity for receiving a surgical tool, and a first locking mechanism moveable between first and second positions relative to the housing, the first locking mechanism including a through hole for receiving the surgical tool.

An aspect of the exemplary embodiment is that the handle assembly further includes a second retaining mechanism attached to a proximal end of the handle. The second retaining mechanism comprises a second retaining housing having a second central cavity for receiving a handle extension, and a second locking mechanism moveable between first and second positions relative to the second retaining housing, the second locking mechanism having a through hole for receiving the handle extension.

Another aspect of the exemplary embodiment is that the first retaining mechanism further includes an alignment tab about a lateral side of the first locking mechanism that limits movement of the first locking mechanism. According to an aspect, the alignment tab directly engages an indentation about a lateral side of the first locking mechanism.

Another aspect of the exemplary embodiment is that the first retaining housing includes a bore adjacent the first central cavity to receive an alignment tab of the first retaining mechanism. Another aspect of the exemplary embodiment is that the first retaining mechanism includes a first biasing member that biases the first locking mechanism towards the first position. According to an aspect, the first biasing member directly engages the first locking mechanism.

Another aspect of the exemplary embodiment is that the first locking mechanism includes a lip that partially occludes the first central cavity when in the first position. Another aspect of the exemplary embodiment is that the through hole of the first locking mechanism is larger than the first central cavity.

Another aspect of the exemplary embodiment is that the second retaining mechanism further includes an alignment tab about a lateral side of the second locking mechanism that limits movement of the second locking mechanism. According to an aspect, the alignment tab directly engages an indentation about a lateral side of the second locking mechanism. Another aspect of the exemplary embodiment is that the second retaining housing includes a bore adjacent the second central cavity to receive an alignment tab of the second retaining mechanism.

Another aspect of the exemplary embodiment is that the second locking mechanism includes a lip that partially occludes the second central cavity from receiving the handle extension. Another aspect of the exemplary embodiment is that the second retaining mechanism includes a second biasing member that biases the second locking mechanism towards the first position. According to an aspect, the second biasing member directly engages the second locking mechanism.

Another aspect of the exemplary embodiment is that the second retaining housing includes a plurality of fillets about its perimeter. According to an aspect, the plurality of fillets circumscribes the second central cavity.

In accordance with the exemplary embodiments, there is provided a handle assembly for a surgical tool including a handle having a distal end for releasably receiving a surgical tool and a proximal end for releasably receiving a handle extension. When the handle assembly is used in combination with an implant extraction surgical tool, the disclosure overcomes one more of the disadvantages referenced above by providing a handle that is capable of receiving a handle extension. In an exemplary embodiment, the handle extension can be a T-handle that enables the user to exert considerable extraction force on the surgical tool whereby the surgical tool can effectively extract an implant.

Other features and advantages of the subject disclosure will be apparent from the following more detail description of the exemplary embodiments.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the present disclosure, there are shown in the drawings exemplary embodiments. It should be understood, however, that the subject application is not limited to the precise arrangements and instrumentalities shown.

DETAILED DESCRIPTION OF THE DISCLOSURE

Figure 1A:
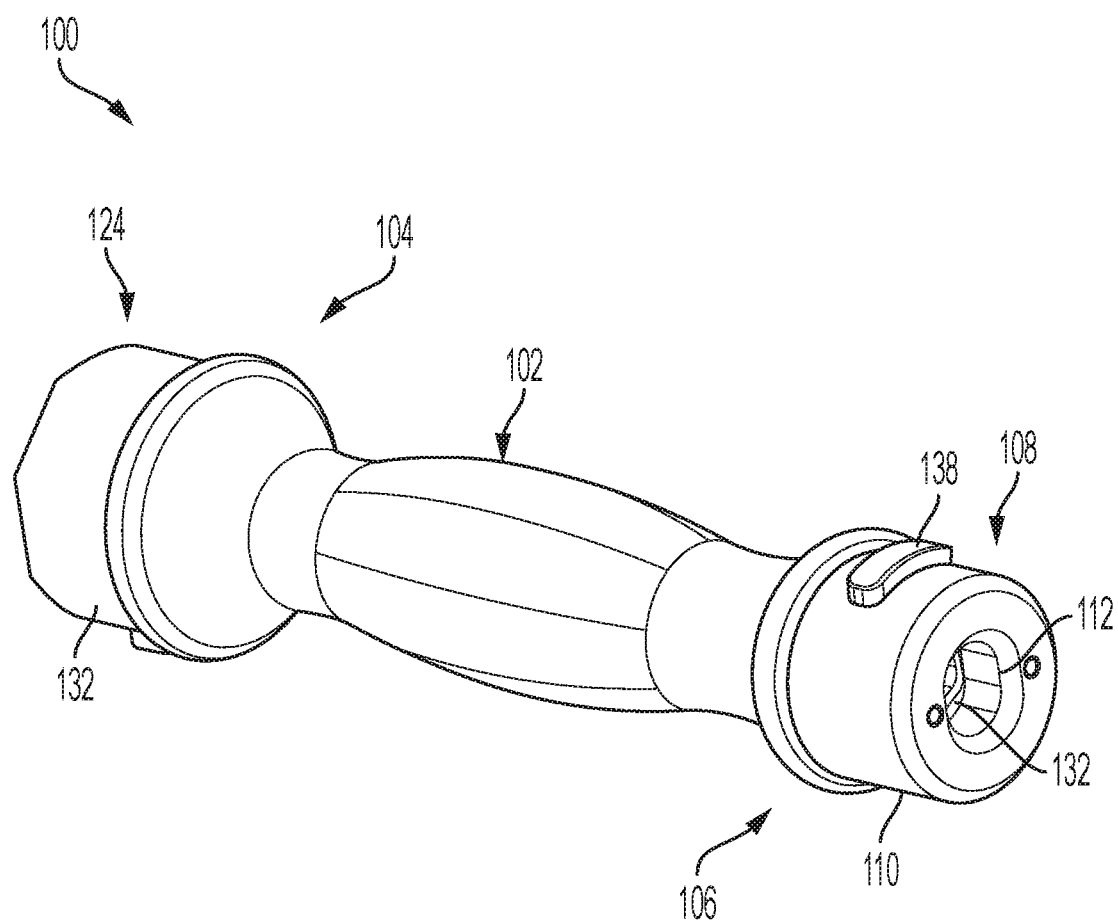
FIG. 1A is a perspective view of a distal end of a handle assembly in accordance with an exemplary embodiment of the subject disclosure.

Reference will now be made in detail to the various exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject application in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Figure 1B:
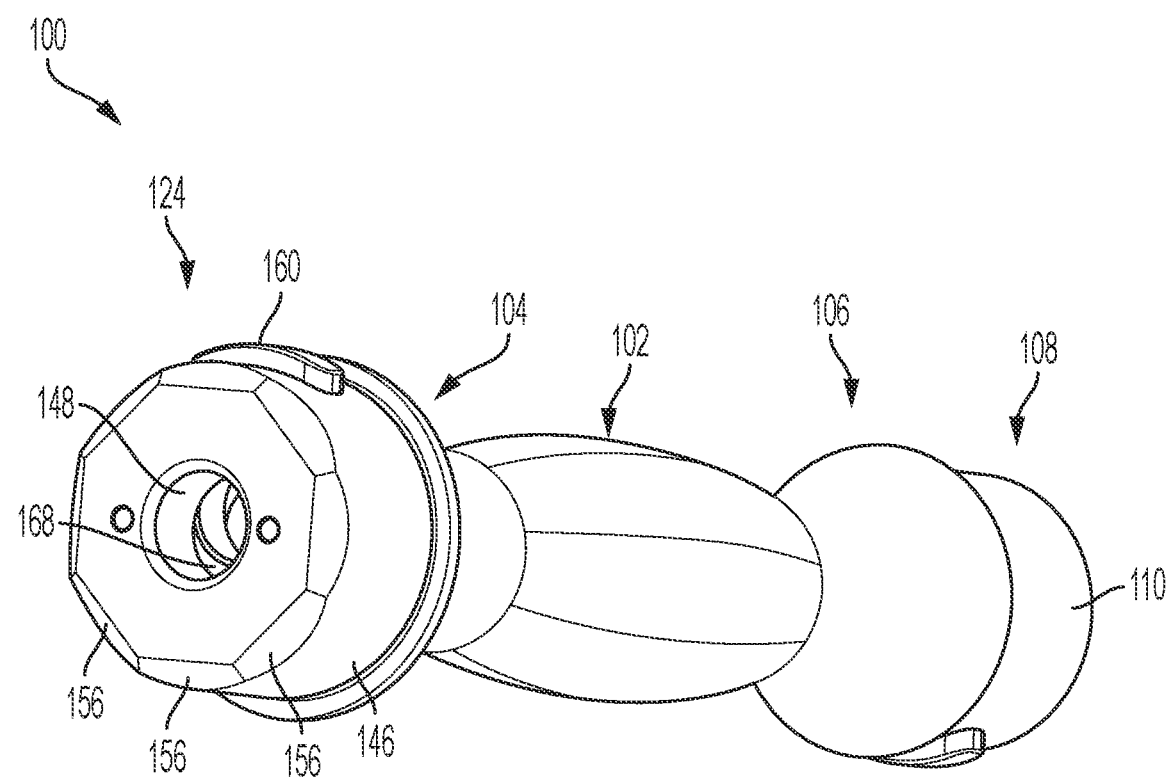
FIG. 1B is a perspective view of a proximal end of the handle assembly of FIG. 1A.
Figure 1C:
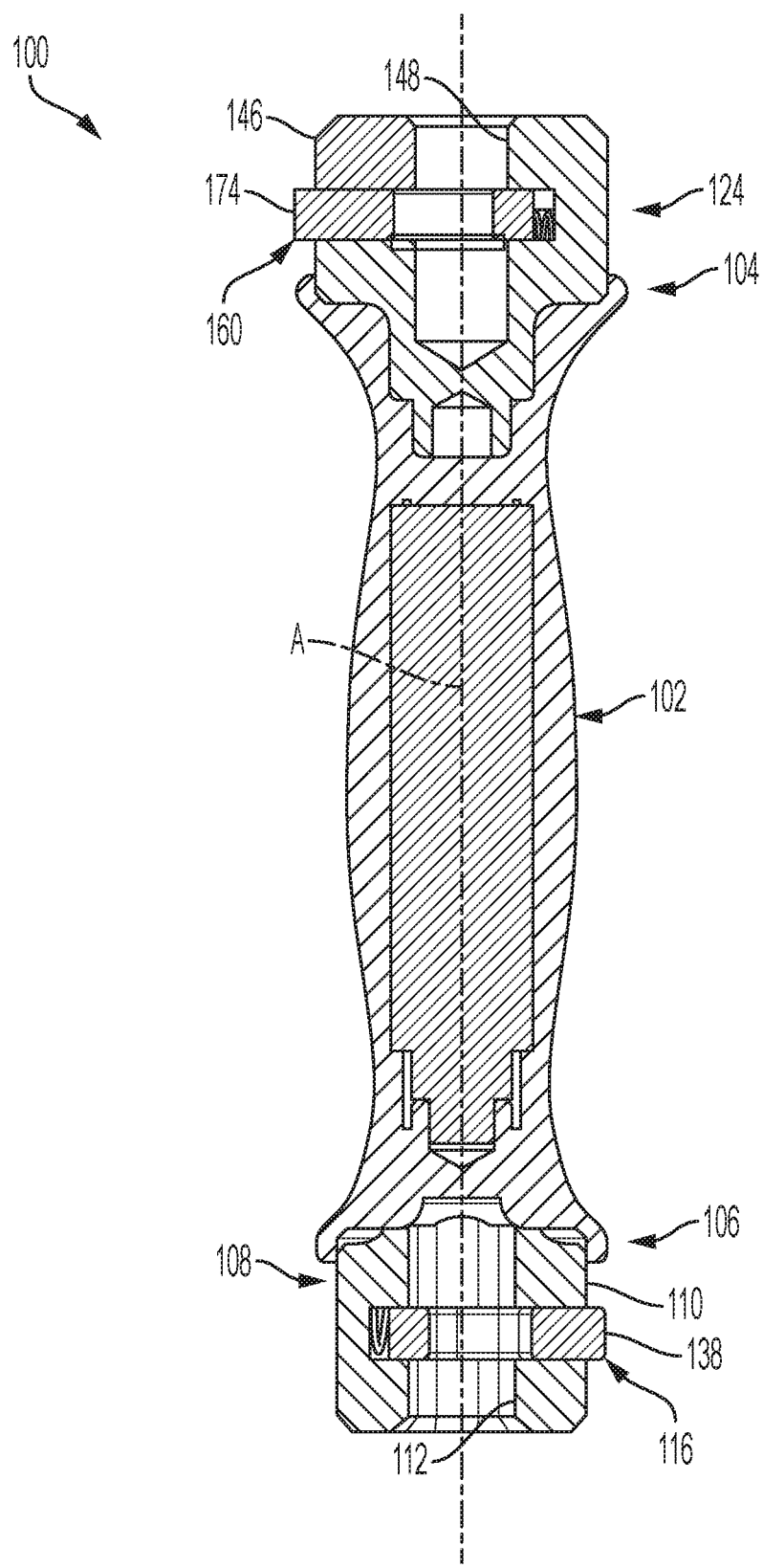
FIG. 1C is a cross-sectional view of the handle assembly of FIG. 1A.

Referring now to the drawings, FIGS. 1A-1C illustrate a handle assembly 100 for a surgical tool in accordance with an exemplary embodiment of the present disclosure. The handle assembly includes a handle 102 having a proximal end 104 and a distal end 106. The handle assembly further includes a first retaining mechanism 108 attached to the distal end of the handle.

Figure 2A:
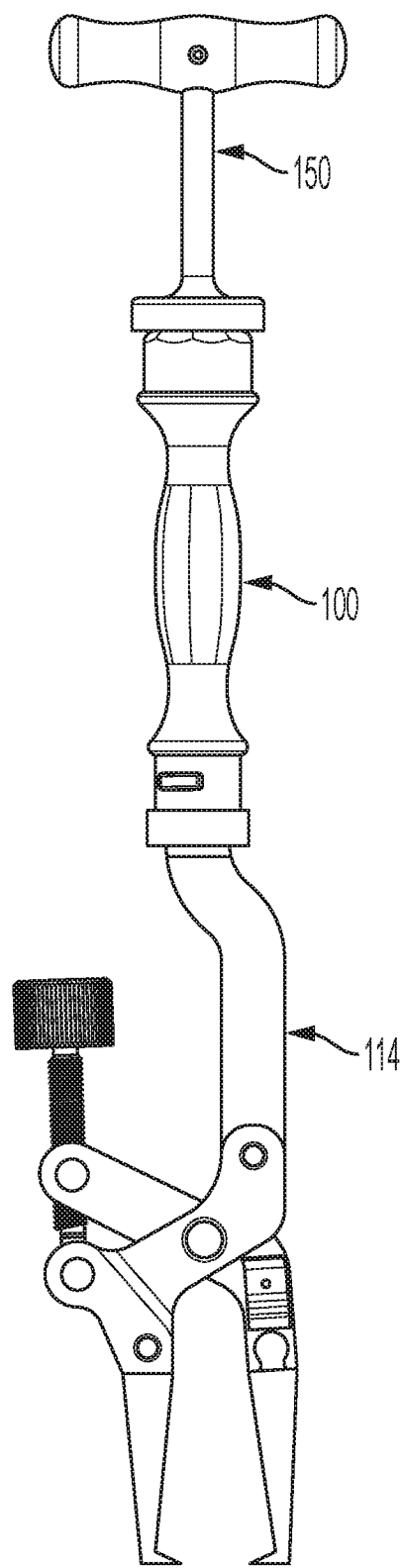
FIG. 2A is an elevational view of a surgical tool and a handle extension attached to the handle assembly of FIG. 1A.
Figure 2B:
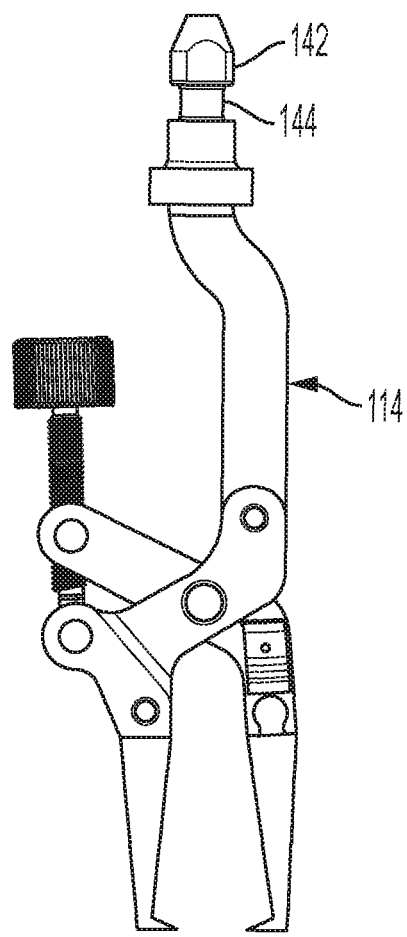
FIG. 2B is an elevational view of the surgical tool of FIG. 2A.
Figure 3A:
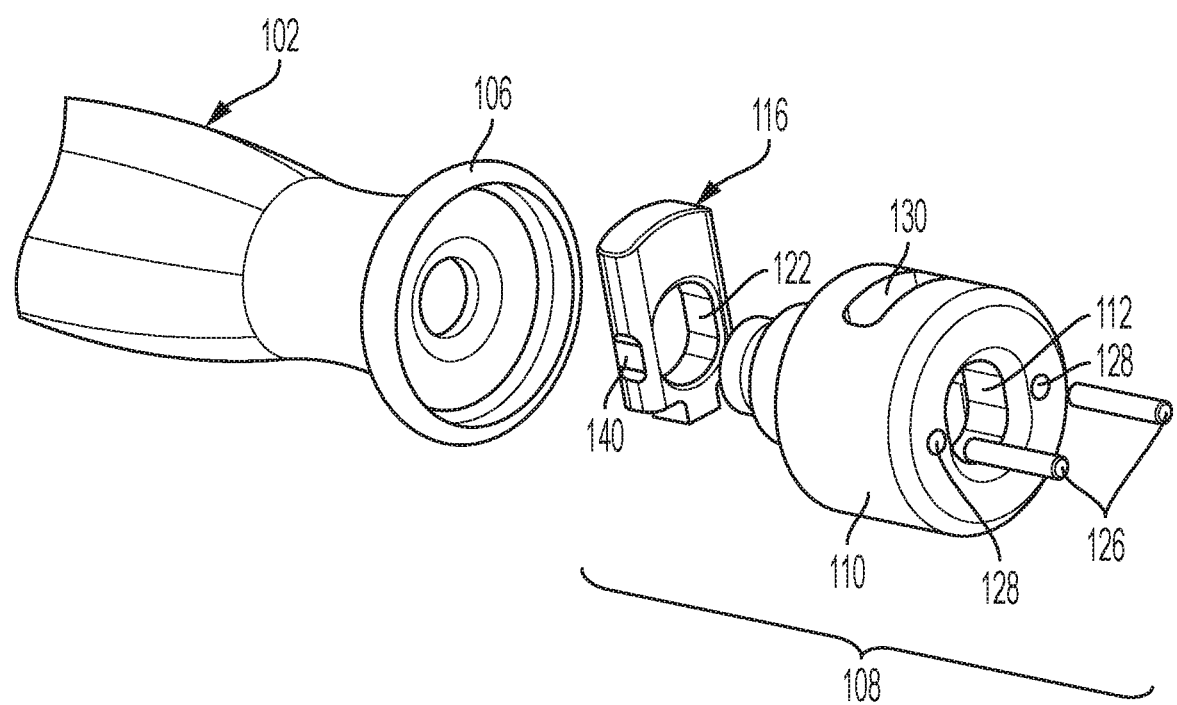
FIG. 3A is an exploded perspective view of the distal end of the handle assembly of FIG. 1A.
Figure 3B:
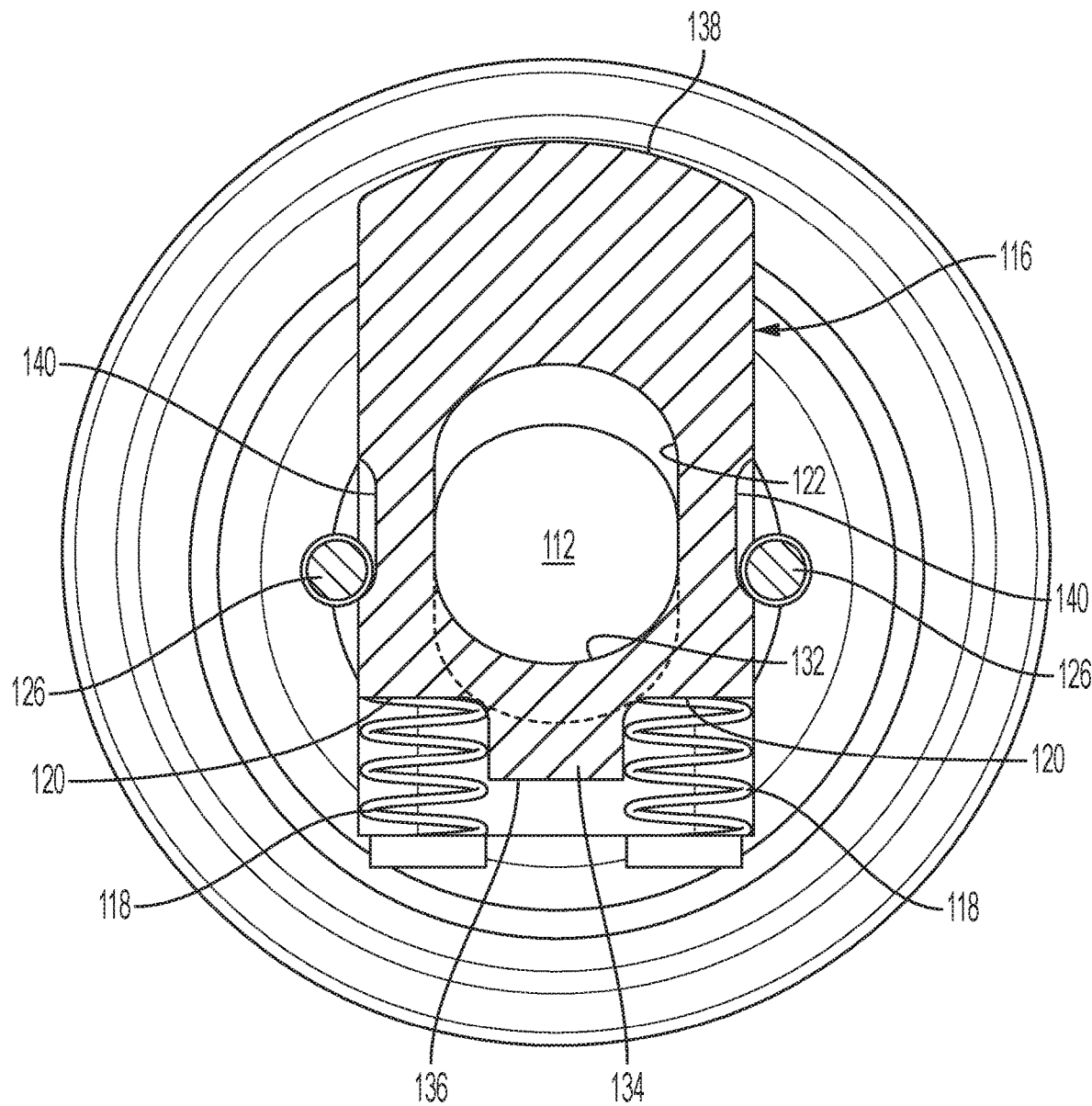
FIG. 3B is a cross-sectional view of a first locking mechanism of a first retaining mechanism of the handle assembly of FIG. 1A in a first position.
Figure 3C:
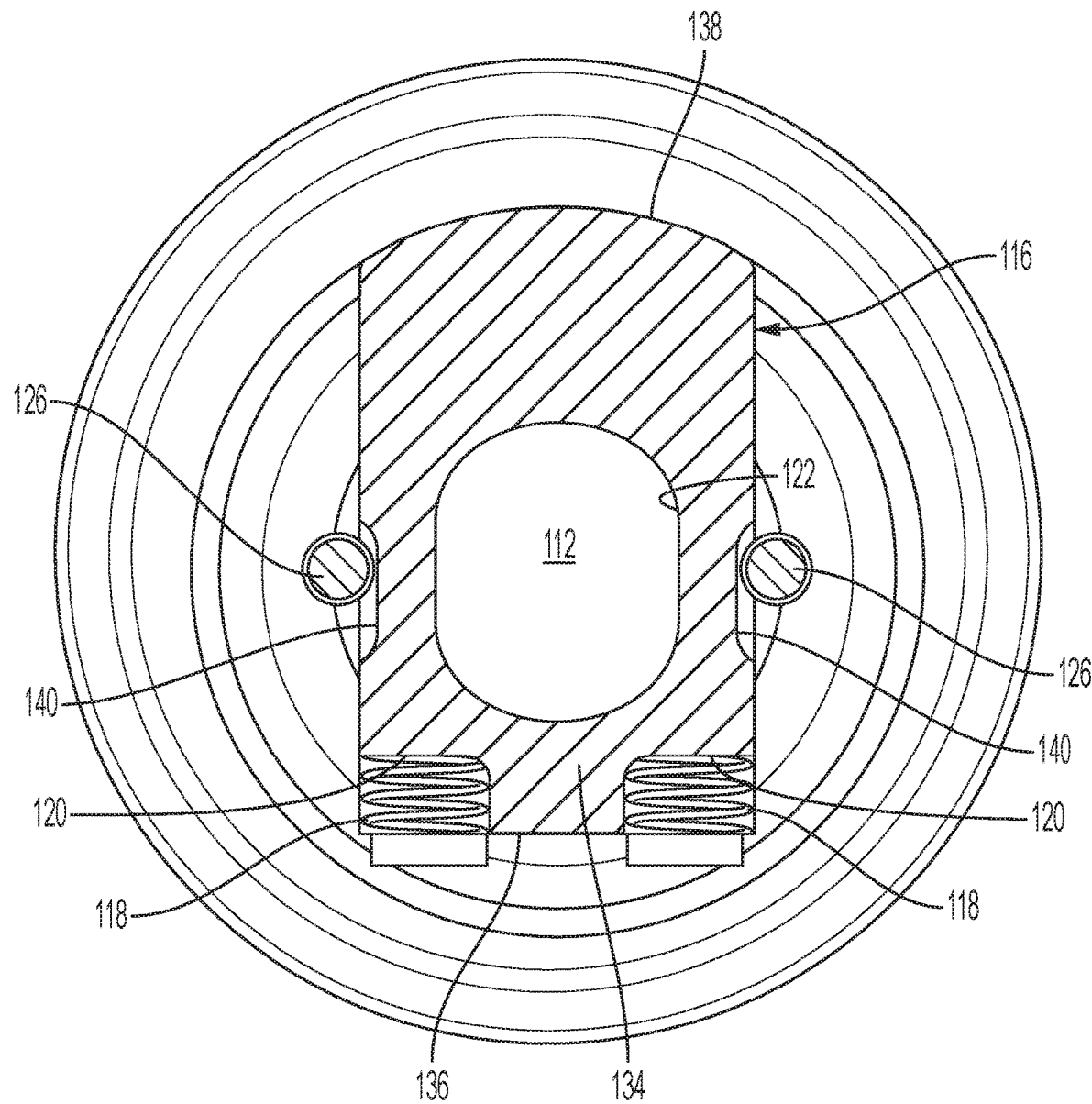
FIG. 3C is a cross-sectional view of the first locking mechanism FIG. 3B in a second position.

As shown in FIGS. 1A, 1C, 3A-3C, 5A and 5B, the first retaining mechanism 108 includes a first retaining housing 110 having a first central cavity 112 for receiving a surgical tool 114 (FIGS. 2A and 2B). Representative surgical tools which can be received in the first central cavity may include, without limitation, a shoulder stem extractor, chisels, threaded extractors and the like. Referring to FIGS. 3A-3C and 6A-6C, the first retaining mechanism further includes a first locking mechanism 116 moveable between first (FIG. 3B) and second (FIG. 3C) positions relative to the first retaining housing. As shown in FIGS. 3B and 3C, the first retaining mechanism includes at least one biasing member 118 e.g., a first biasing member 118 engageable with at least one lateral shoulder 120 of the first locking mechanism for biasing the first locking mechanism into the first position. The first locking mechanism includes a through hole 122 for receiving the surgical tool. As illustrated, the first central cavity 112 and through hole 122 have an elongate or substantially oval shape, although they may assume other suitable shapes including, without limitation, circular. According to an aspect, the through hole of the first locking mechanism can be larger than the first central cavity.

FIGS. 1A and 1B show that the handle 102 is preferably relatively larger in a central region thereof, tapers from the central region towards the proximal and distal ends, and is enlarged at the proximal and distal ends. So constructed, the handle provides an ergonomically comfortable shape for the user's hand while having distal and proximal ends of sufficient size to respectively attach the first retaining mechanism 108 and a second retaining mechanism 124 (described below) to the handle.

Referring to FIGS. 3A-3C, the first retaining mechanism 108 further includes an alignment tab, e.g. an alignment dowel 126 about a lateral side of the first locking mechanism that limits movement of the first locking mechanism, as further described below. The alignment tab can alternatively be a square or rectangular rod, or a rod with an oval or triangular longitudinal cross-section.

Figure 5A:
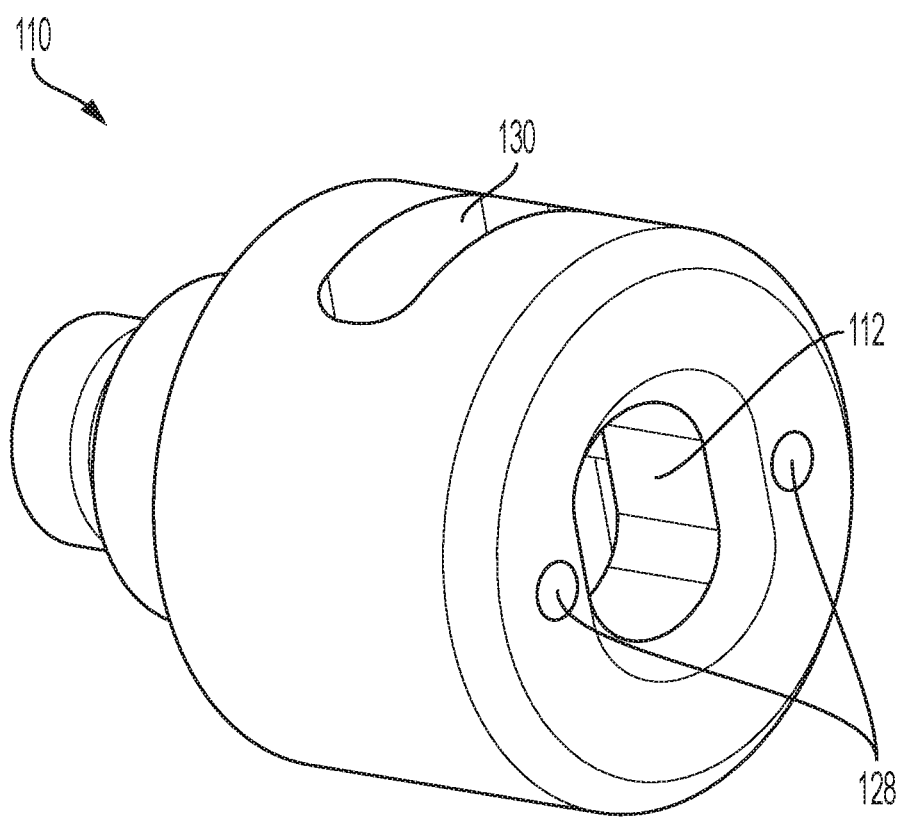
FIG. 5A is a perspective view of a distal end of a first retaining housing of the handle assembly of FIG. 1A.
Figure 5B:
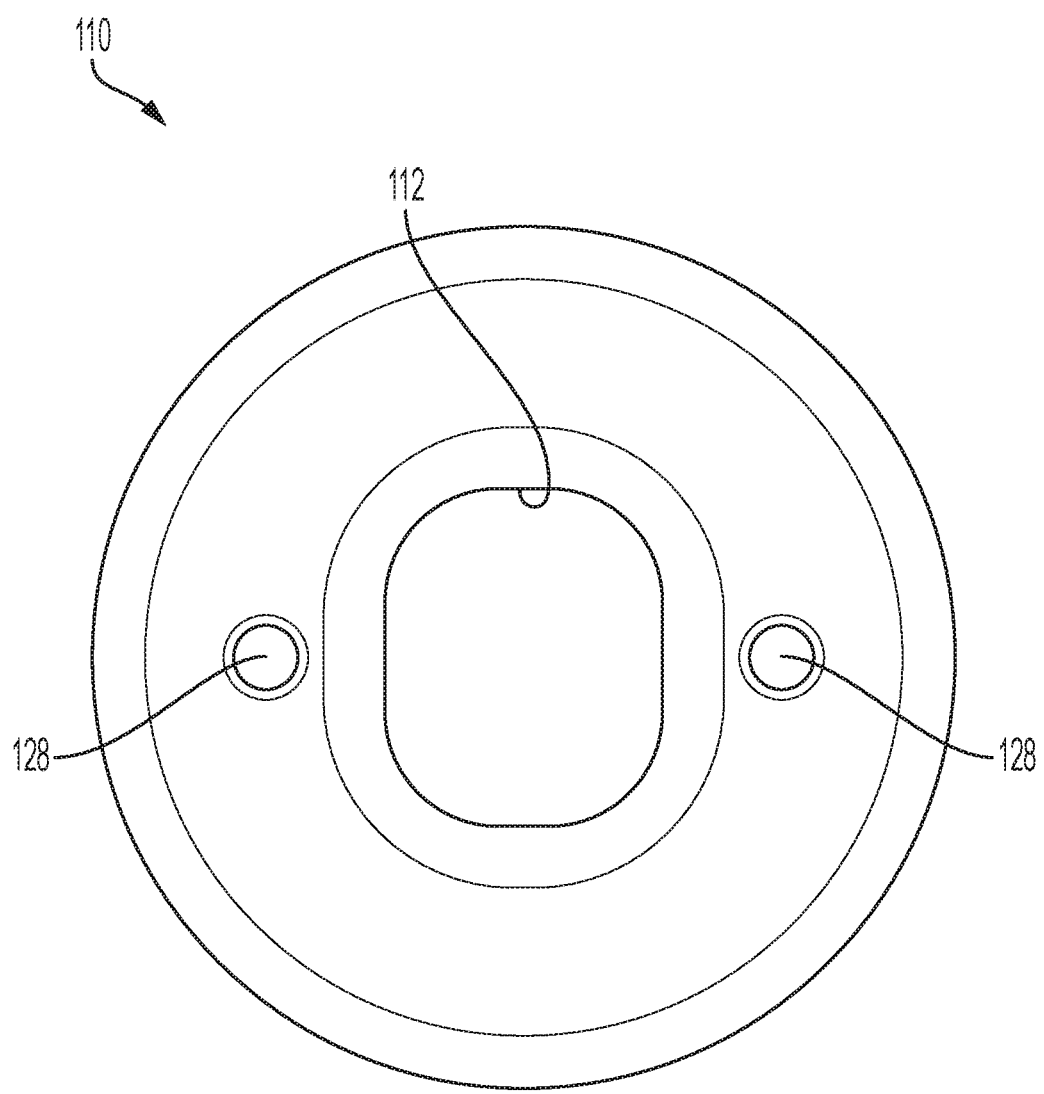
FIG. 5B is an end view of the distal end of the first retaining housing of FIG. 5A.

FIGS. 3A, 5A and 5B show that the first retaining housing 110 includes a bore 128 adjacent the first central cavity 112 to receive the alignment tab 126. In the illustrated exemplary embodiment, the first retaining housing includes a pair of bores 128 adjacent the first central cavity to receive a pair of alignment tabs 126. The pair of bores are positioned about opposite lateral sides of the first locking mechanism 116, and are distally facing e.g., the bore openings are distally facing.

FIGS. 3A and 5A show that the first retaining housing further includes an opening 130 for slidably receiving the first locking mechanism 116. The opening 130 opens about a lateral side of the first retaining housing 110 and is positioned i.e., has a longitudinal extent that extends substantially perpendicular to and between the bores 128 e.g., the longitudinal axes of the bores.

Figure 6A:
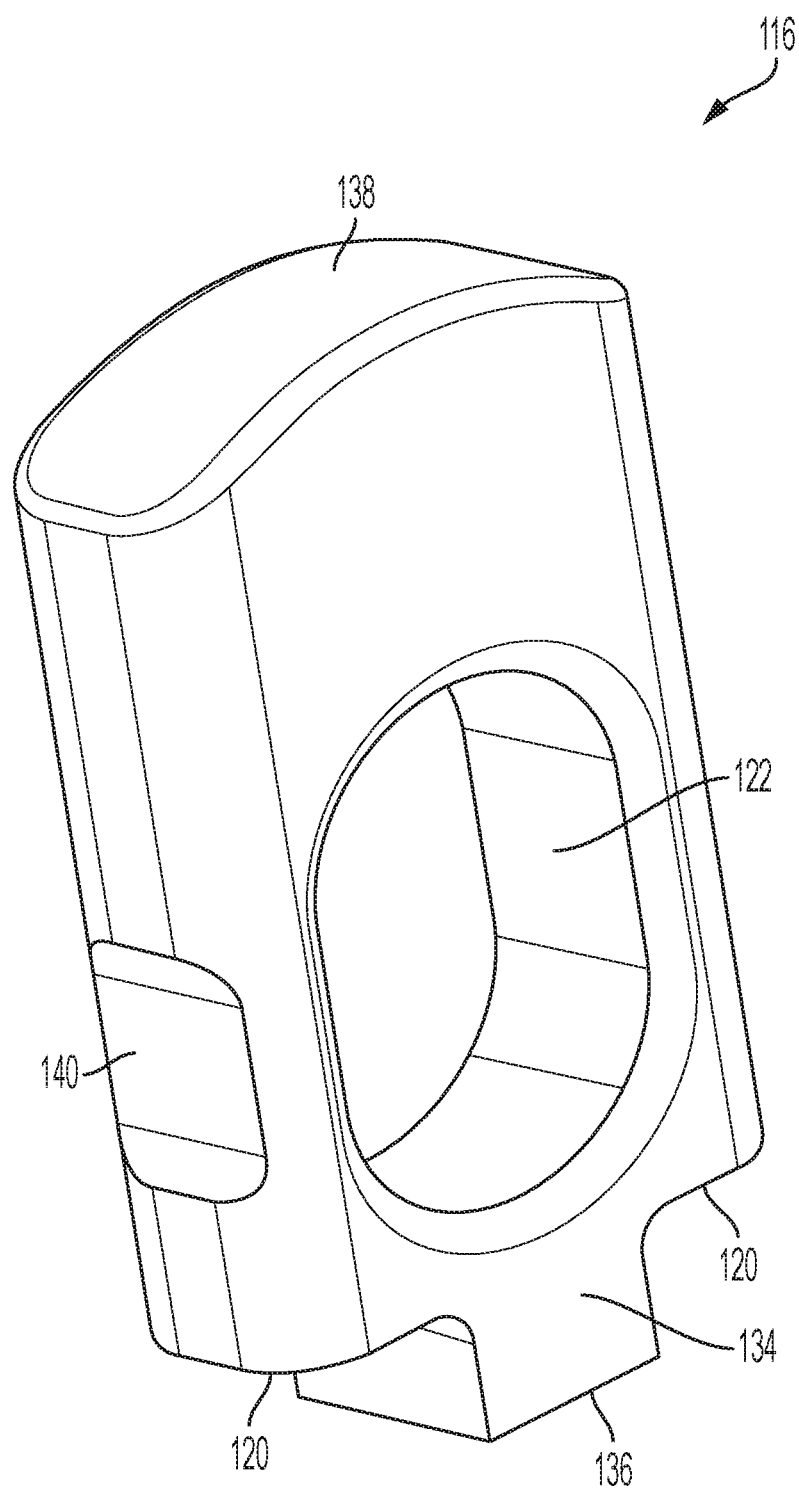
FIG. 6A is a top perspective view of a first locking mechanism of the handle assembly of FIG. 1A.
Figure 6B:
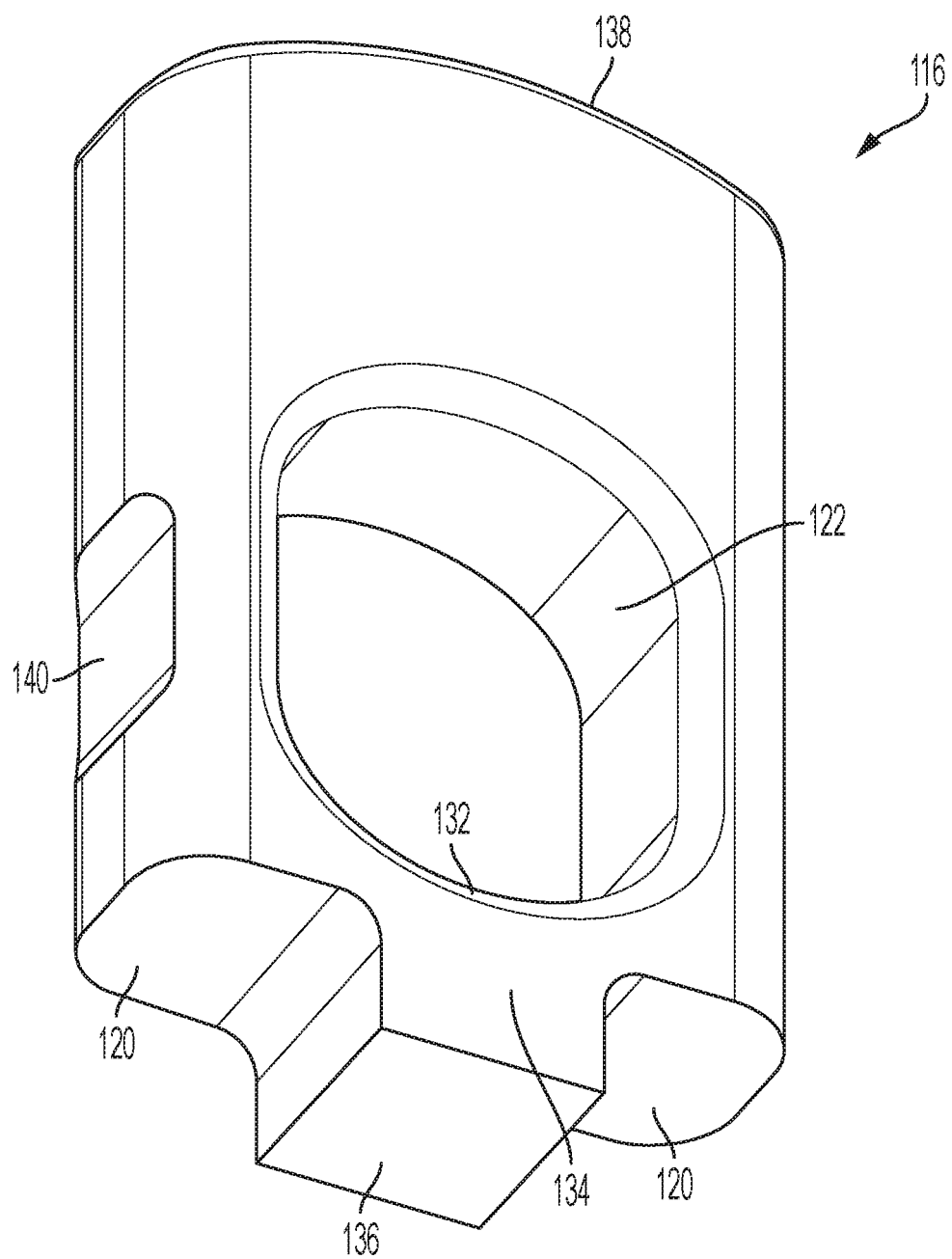
FIG. 6B is a bottom perspective view of the first locking mechanism of FIG. 6A.

The first locking mechanism 116 is configured as best shown in FIGS. 3B, 3C and 6A-6C. The first locking mechanism has an elongated shape with the through hole 122 situated generally centrally thereof. As best shown in FIGS. 1A, 3B and 6B, the first locking mechanism 116 further includes a lip 132 that partially occludes the first central cavity 112 when in the first position. The lip 132 is formed as part of the perimeter of the through hole 122. More particularly, the lip 132 is that part of the perimeter of the through hole 122 that projects into the first central cavity by virtue of the first biasing member(s) 118 pushing against the lateral shoulders 120 whereby the first locking mechanism 116 assumes the first position.

At a first end 134 of the first locking mechanism there is provided a centrally located projection 136 that separates the lateral shoulders 120. The projection 136 functions as a stop for the first locking mechanism within the first retaining housing when the first locking mechanism is in the second position (FIG. 3C) relative to the first retaining housing. The first locking mechanism includes a second end or button end 138 opposite the first end that is selectively depressed by a user to move the first locking mechanism from the first position (FIG. 3B) to the second position (FIG. 3C), as described in greater detail below.

The first biasing member(s) 118 bias the first locking mechanism 116 into the first position. That is, first ends of the biasing member(s) 118 abut a surface of the first retaining housing and second ends of the first biasing member(s) abut the lateral shoulders 120 whereby the first biasing member(s) urge the first locking mechanism 1116 into the first position. The first biasing member(s) 118 can be e.g., compression springs, rubber or other elastomeric members capable of being compressed when a user depresses the second end 138 of the first locking mechanism to urge the first locking mechanism to the second position and capable of returning the first locking mechanism to the first position upon a user releasing the second end 138.

Figure 6C:
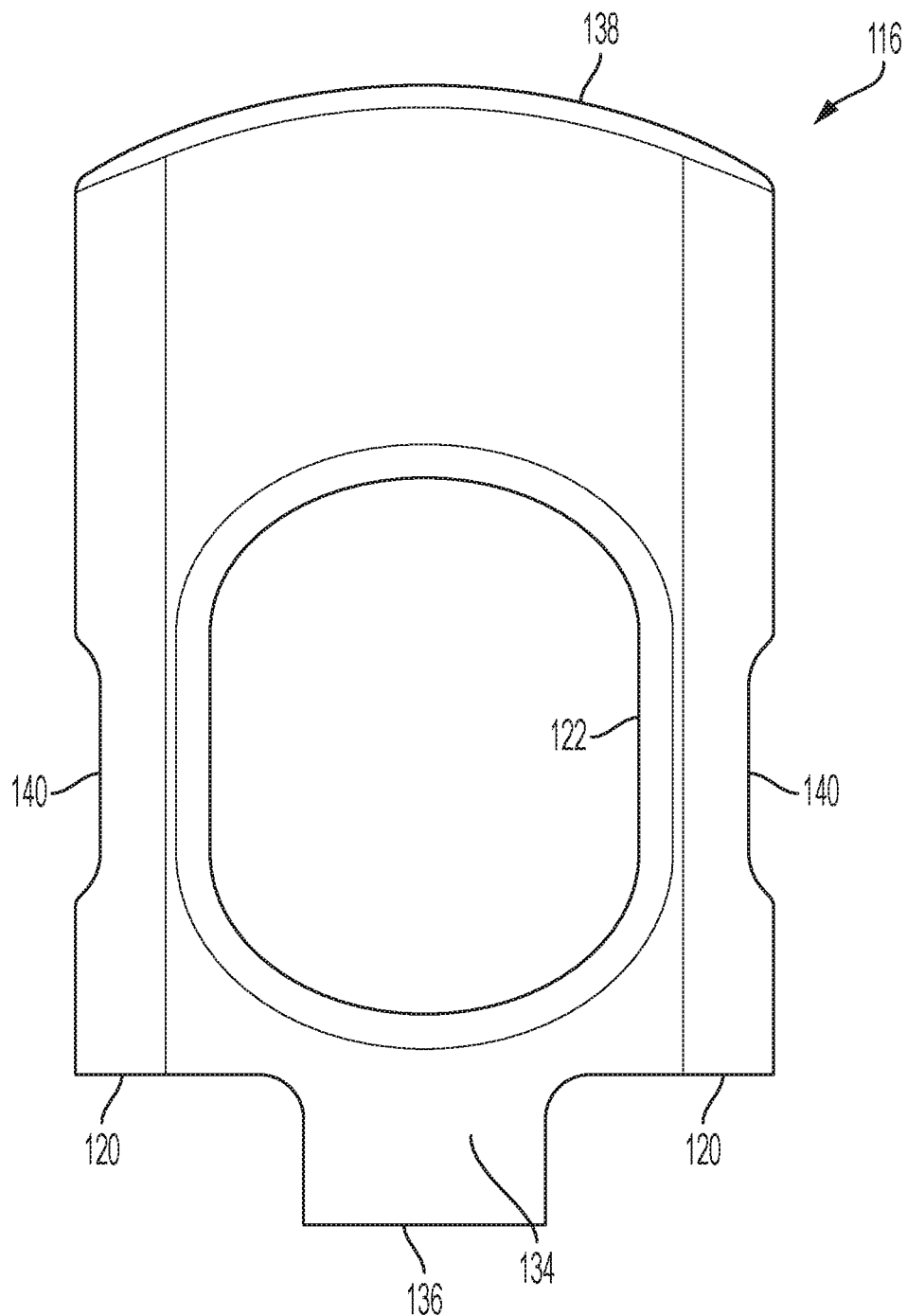
FIG. 6C is an elevational view of the first locking mechanism of FIG. 6A.

FIGS. 6A-6C show that the first locking mechanism 116 further includes at least one indentation 140 about a lateral side thereof. FIGS. 3A, 3B show that each alignment tab 126 directly engages an indentation 140. In the illustrated exemplary embodiment, the first retaining mechanism includes a pair of alignment tabs 126 about opposite lateral sides of the first locking mechanism directly engaging a corresponding pair of indentations 140 about opposite lateral sides of the first locking mechanism.

By way of illustration, but not limitation, one can first attach the surgical tool 114 to the first retaining housing 110 of the first retaining mechanism 108 at the distal end 106 of the handle 102. To do so, the user depresses the button end 138 of the first locking mechanism 116 that projects outwardly from the first retaining housing 110 (FIGS. 1A, 3B) against the bias of the first biasing member(s) 118 until the lip 132 no longer partially occludes the first central cavity 112 and the through hole 122 of the first locking mechanism is in substantial alignment with the first central cavity (FIG. 3C). The user then inserts a male connector 142 of the surgical tool 114 (FIG. 2B) through the first central cavity 112 and the through hole 122 and releases the button end 138 of the first locking mechanism 116. The first biasing member(s) 118 thus exert force against the lateral shoulders 120 thereby urging the lip 132 of the first locking mechanism to engage a reduced diameter neck 144 adjacent the male connector of the surgical tool and lock the surgical tool to the first retaining mechanism 108.

As the lip 132 moves from the occluding first position to the non-occluding second position and back again, the indentation(s) 140 of the first locking mechanism 116 move relative to the alignment tab(s) 126. However, the opposite ends of the indentation(s) serve as stops to control the range of movement of the first locking mechanism 116 relative to the first retaining housing 110.

Figure 2C:
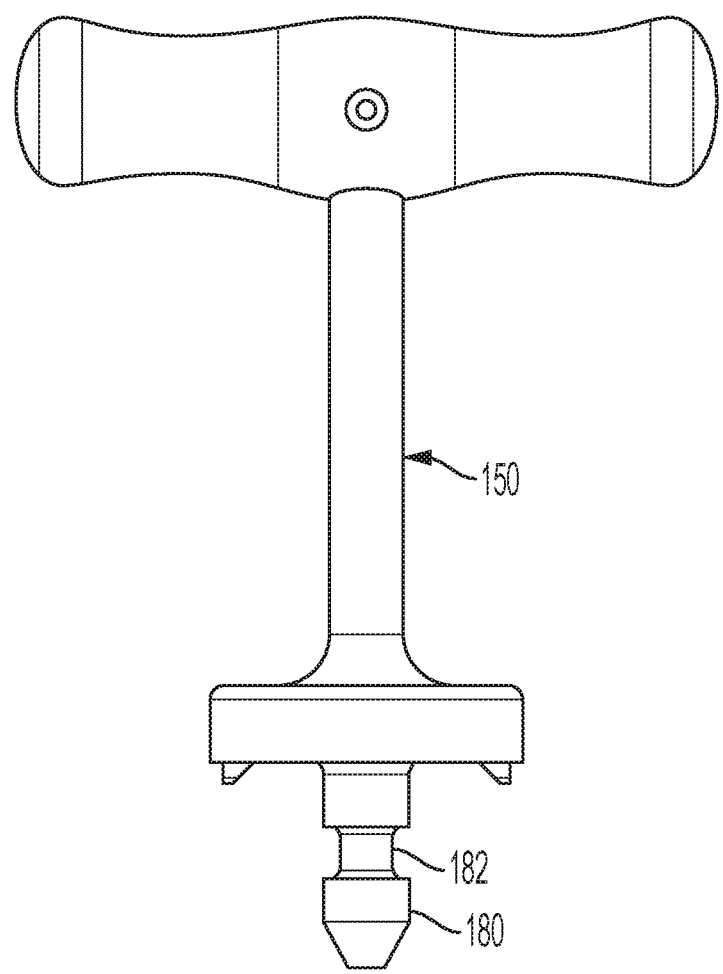
FIG. 2C is an elevational view of the handle extension of FIG. 2A.

Referring to FIGS. 1A and 1B, the handle assembly 100 further comprises the second retaining mechanism 124 attached to the proximal end 104 of the handle 102. As shown in FIGS. 1B, 1C, 4A, 4B, 7A and 7B, the second retaining mechanism includes a second retaining housing 146 having a second central cavity 148 for receiving a handle extension 150 (FIGS. 2A and 2C). Representative handle extensions that can be received in the second central cavity may include, without limitation, a T-handle, a hammer wing, an extended wing, a slap hammer, and the like.

Figure 4A:
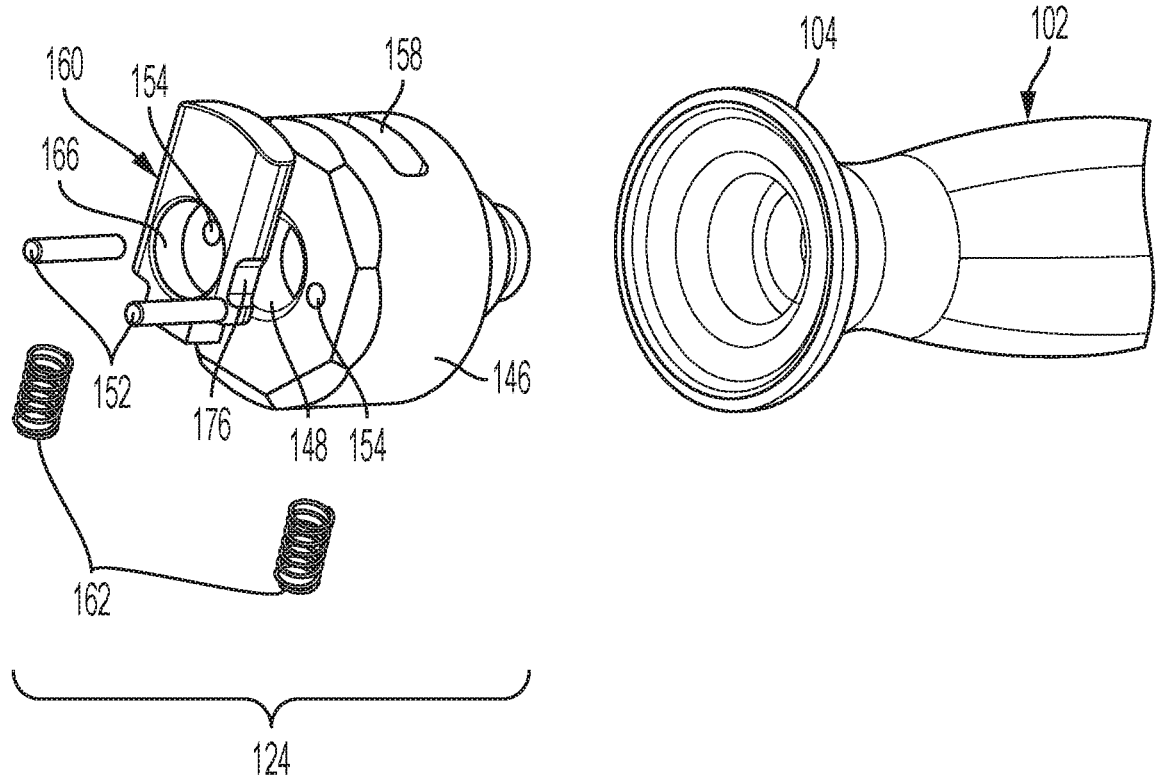
FIG. 4A is an exploded perspective view of the proximal end of the handle assembly of FIG. 1A.
Figure 4B:
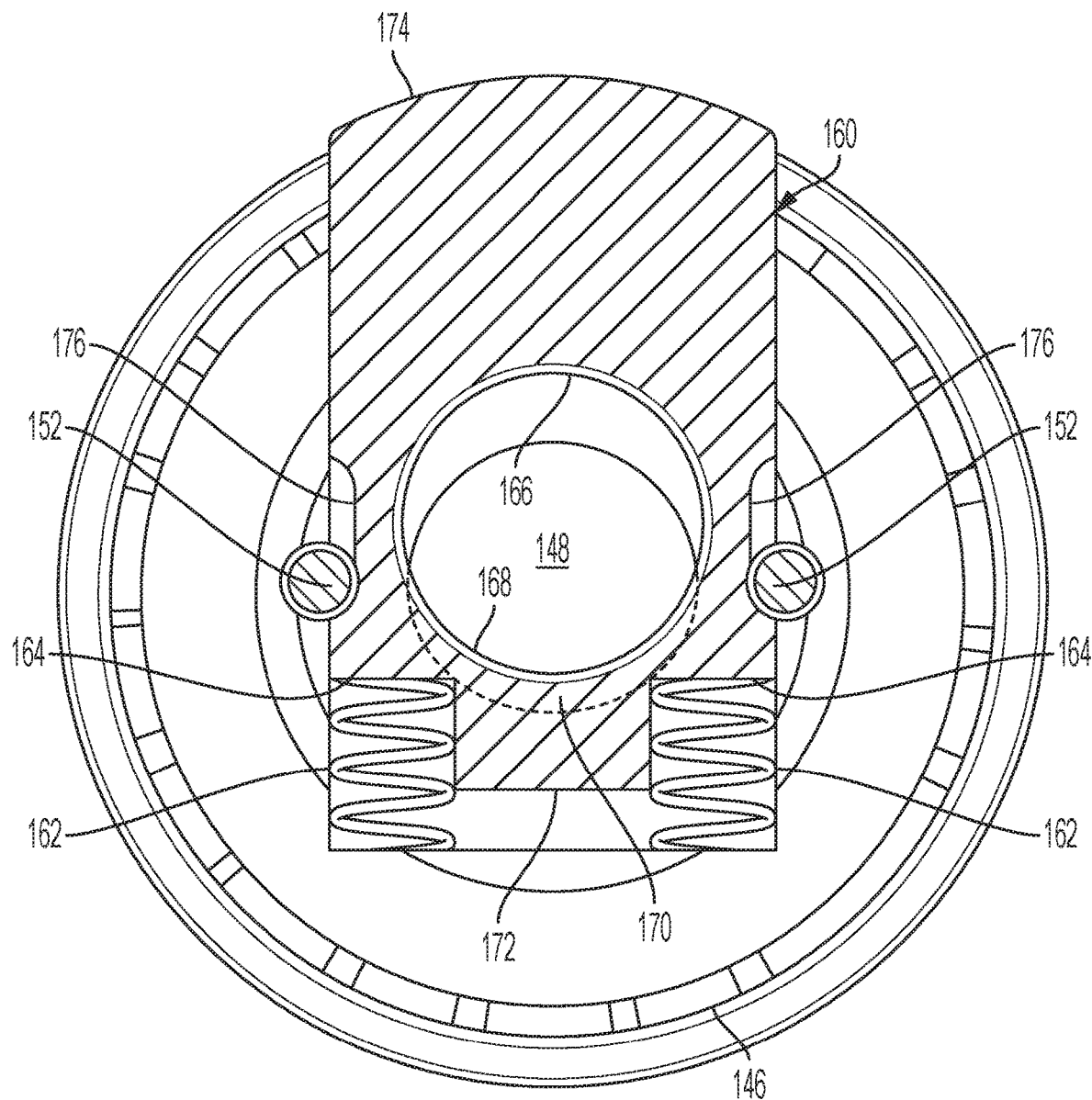
FIG. 4B is a cross-sectional view of a second locking mechanism of a second retaining mechanism of the handle assembly of FIG. 1A in a first position.

Referring to FIGS. 4A and 4B, the second retaining mechanism 124 includes an alignment tab, e.g., an alignment dowel 152 about a lateral side of the second locking mechanism that limits movement of the second locking mechanism, as described below. The alignment tab can alternatively be a square or rectangular rod, or a rod with an oval or triangular longitudinal cross-section. Preferably, the second retaining mechanism 124 includes a pair of alignment dowels about opposite lateral sides of the second locking mechanism.

Figure 7A:
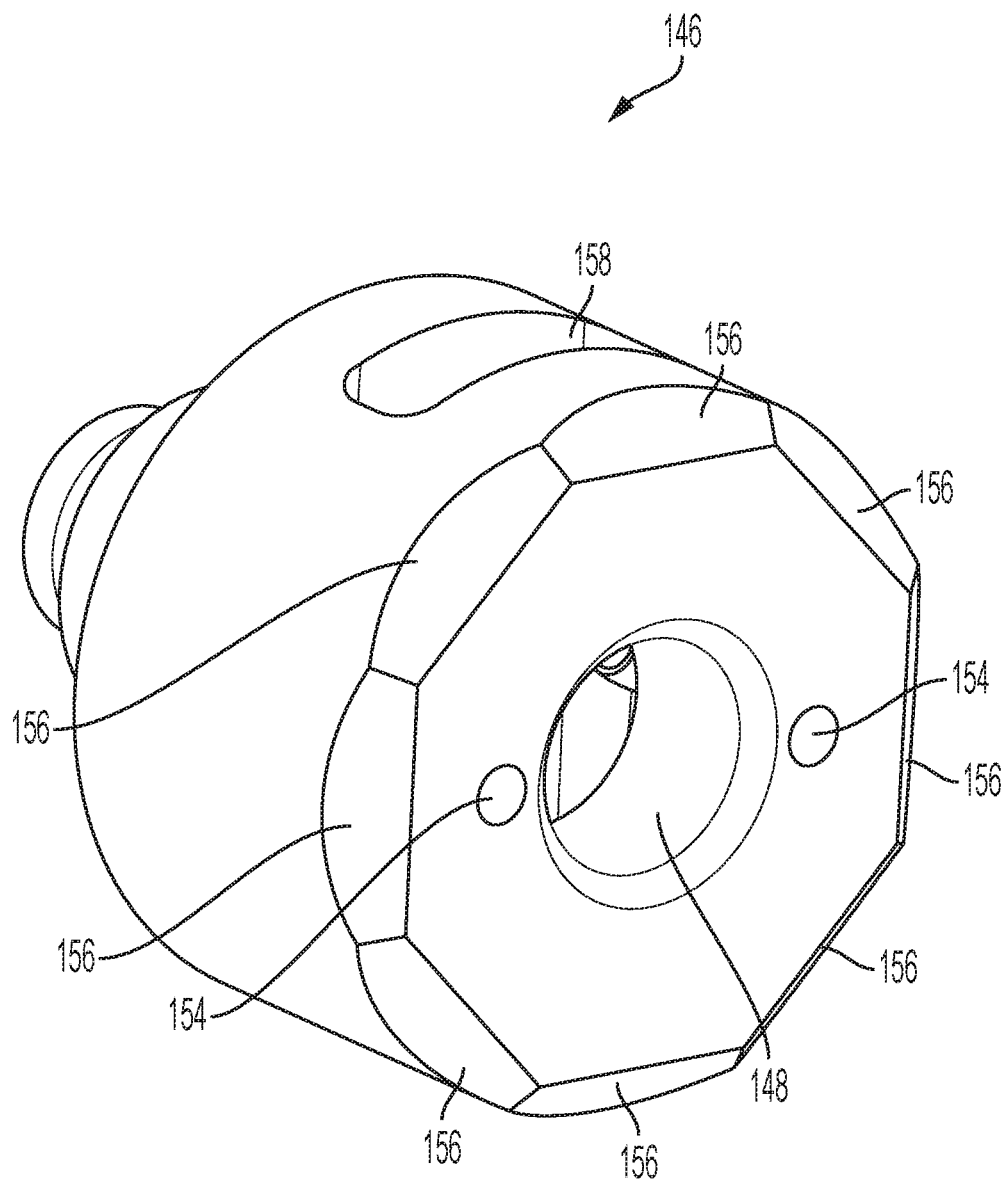
FIG. 7A is a perspective view of a proximal end of a second retaining housing of the handle assembly of FIG. 1A.
Figure 7B:
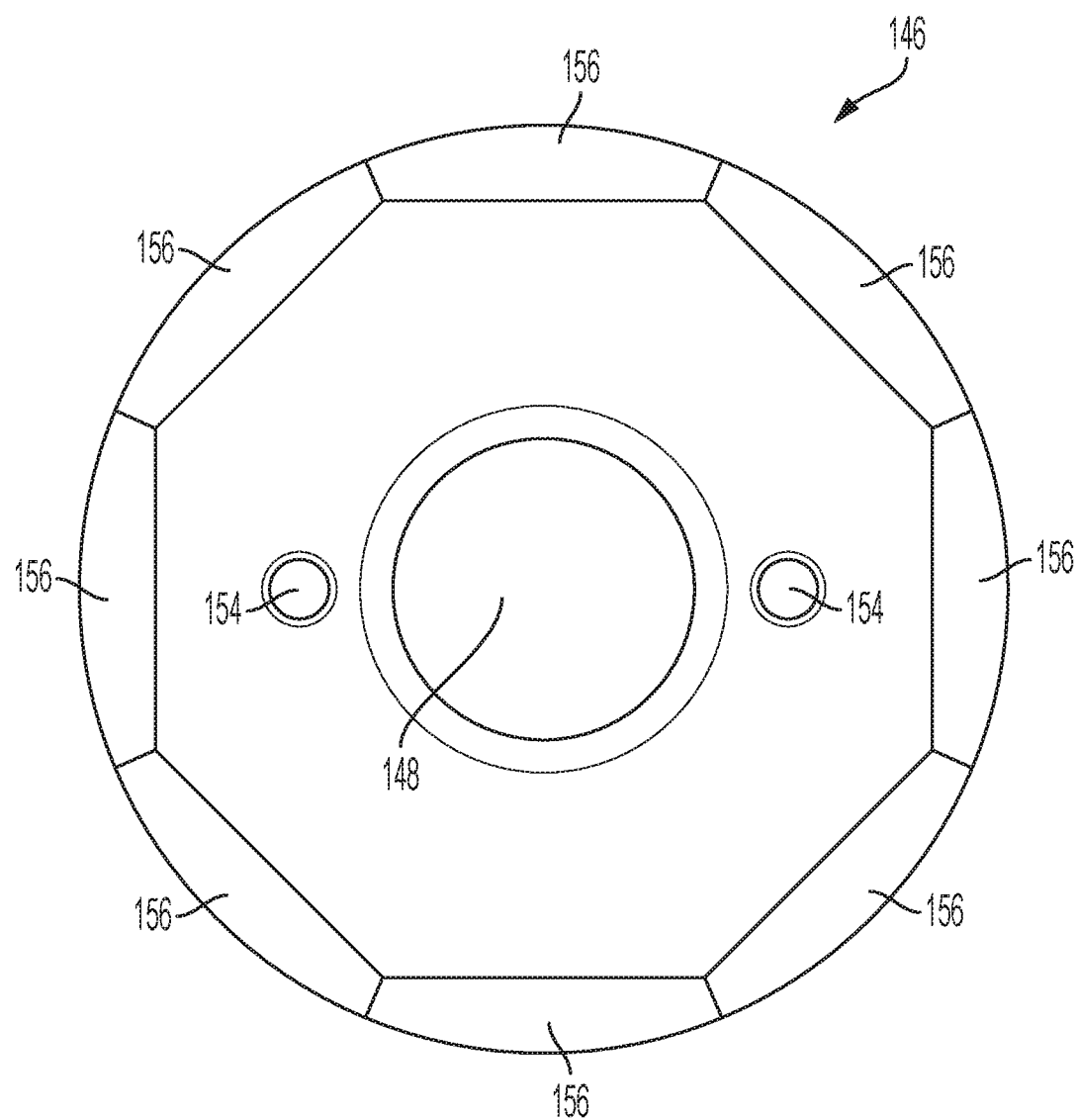
FIG. 7B is an end view of the proximal end of the second retaining housing of FIG. 7A.
Figure 8A:
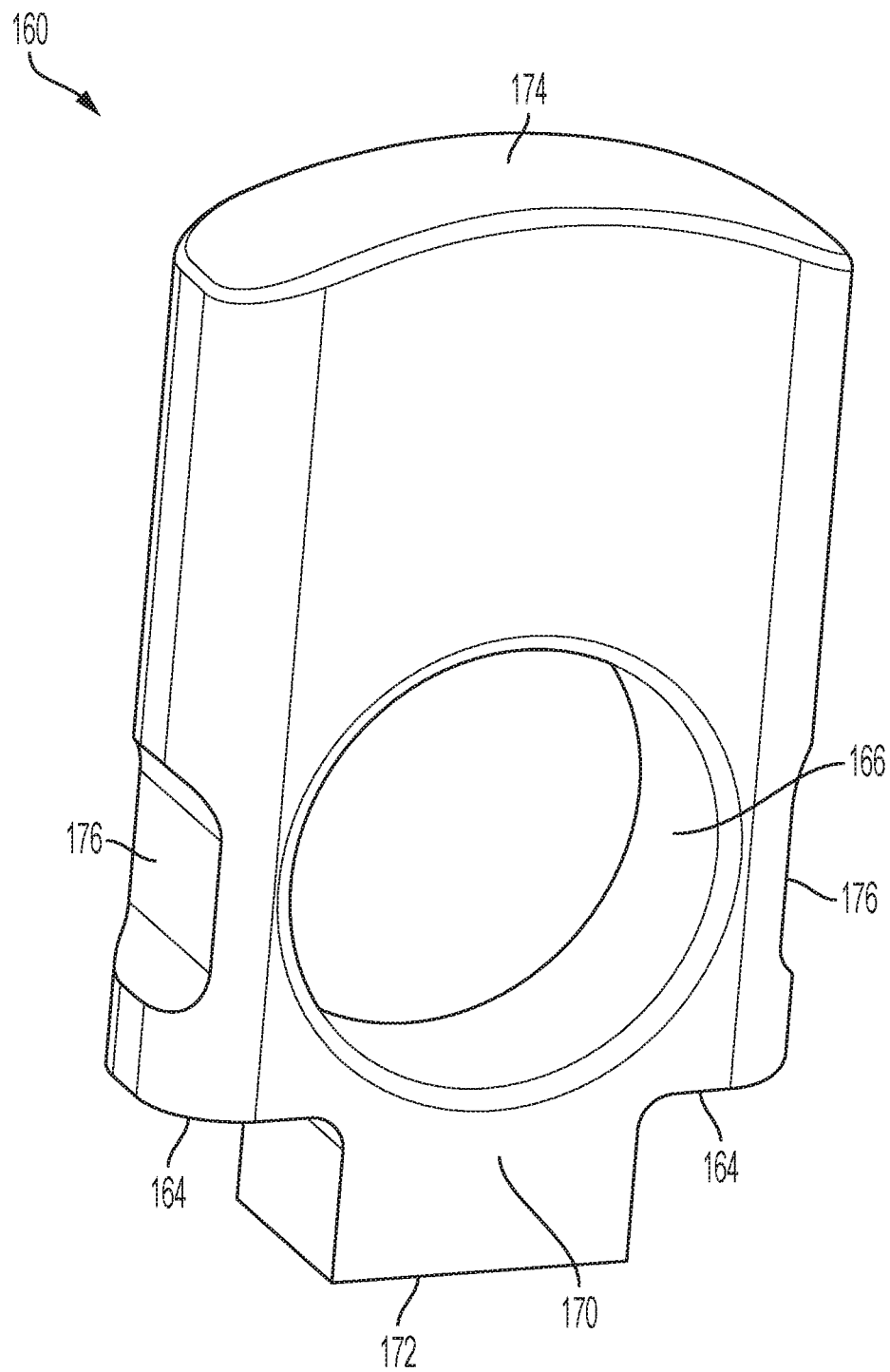
FIG. 8A is a top perspective view of a second locking mechanism of the handle assembly of FIG. 1A.
Figure 8B:
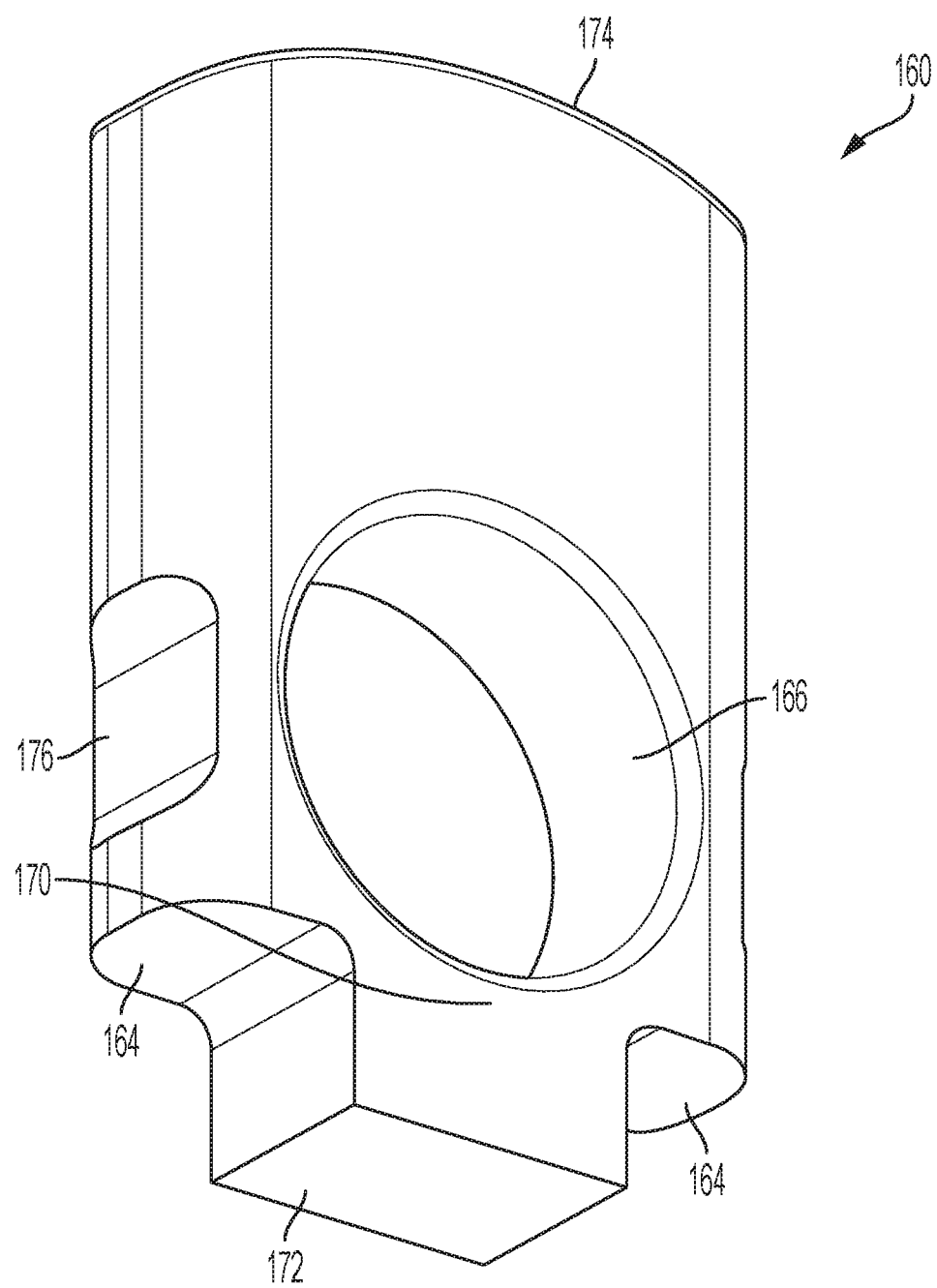
FIG. 8B is a bottom perspective view of the second locking mechanism of FIG. 8A.
Figure 8C:
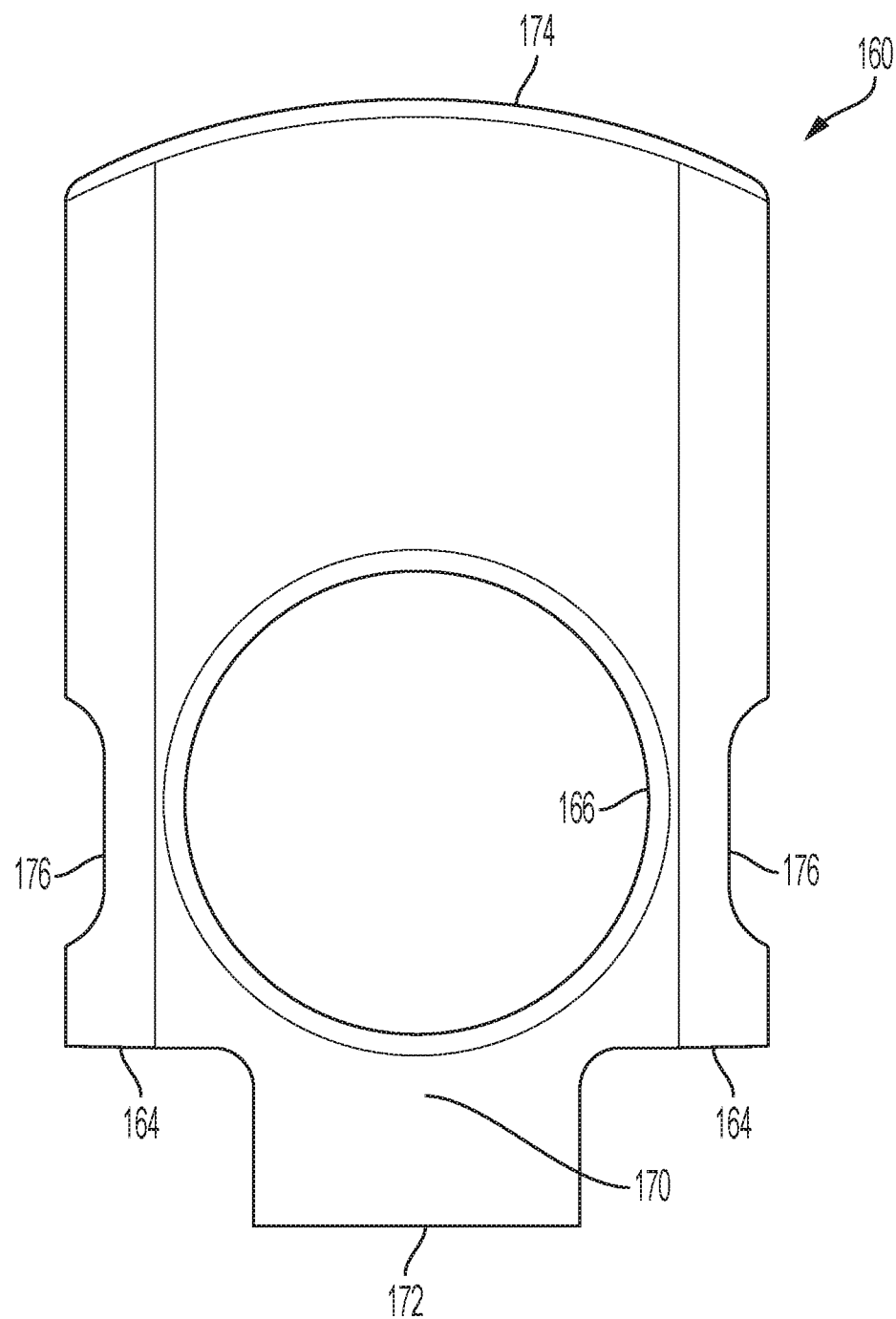
FIG. 8C is an elevational view of the second locking mechanism of FIG. 8A.

FIGS. 4A, 7A and 7B show that the second retaining housing 146 includes a bore 154 adjacent the second central cavity 148 to receive the alignment tab 152. In the illustrated embodiment, the second retaining housing includes a pair of bores 154 adjacent the second central cavity to receive a pair of the alignment tabs 152. The second retaining housing further includes a plurality of fillets 156 about its periphery which, according to an aspect, circumscribe the second central cavity 148.

FIGS. 4A and 7A show that the second retaining housing further includes an opening 158 for slidably receiving a second locking mechanism 160 (FIGS. 4A, 4B and 8A-8C) moveable between a first position (FIG. 4B) and a second position relative to the second retaining housing. The opening 158 opens about a lateral side of the second retaining housing 146 and is positioned e.g., such that its longitudinal extent is substantially perpendicular to and between the bores 154, e.g., a longitudinal axis of the bores.

As shown in FIGS. 4A and 4B, the second retaining mechanism includes at least one biasing member 162 that biases the second locking mechanism towards the first position. In the exemplary embodiment, the second retaining mechanism includes a pair of biasing members 162. The biasing member directly engages the second locking mechanism, e.g., the biasing member is engageable with at least one lateral shoulder 164 (FIGS. 4B and 8A-8C) of the second locking mechanism for biasing the second locking mechanism towards the first position. The second locking mechanism includes a through hole 166 for receiving the handle extension. As illustrated, the second central cavity 148 and the through hole 166 have a circular shape, although they may assume other shapes including, without limitation, an elongate or substantially oval shape.

The second locking mechanism 160 is best shown in FIGS. 4B and 8A-8C. The second locking mechanism has an elongated shape with the through hole 166 situated generally centrally thereof. According to an aspect, the through hole 166 of the second locking mechanism can be larger than the second central cavity 148 of the second retaining housing. As best shown in FIG. 4B, the second locking mechanism 160 further includes a lip 168 that partially occludes the second central cavity when in the first position. The lip 168 is formed as part of the perimeter of the through hole 166. More particularly, the lip 168 is that part of the perimeter of the through hole 166 that projects into the second central cavity by virtue of the second biasing member(s) 162 pushing against the lateral shoulders 164 whereby the second locking mechanism 160 assumes the first position.

At a first end 170 of the second locking mechanism there is provided a centrally located projection 172 that separates the lateral shoulders 164. The projection 172 functions as a stop for the second locking mechanism within the second retaining housing when the second locking mechanism is in the second position relative to the second retaining housing. The second locking mechanism includes a second end or button end 174 opposite the first end 170 that is selectively depressed by a user to move the second locking mechanism from the first position (FIG. 4B) i.e., a locking position to the second position i.e., an unlocking or retracted position, as described in greater detail below. As noted above, the second biasing member(s) 162 bias the second locking mechanism 160 into the first position. That is, first ends of the biasing member(s) 162 abut a surface of the second retaining housing and second ends of the second biasing member(s) abut the lateral shoulders 164 whereby the second biasing member(s) urge the second locking mechanism 160 into the first position thereby locking a handle extension thereto.

As shown in FIG. 4B, the alignment tab 152 directly engages an indentation 176 about a lateral side of the second locking mechanism. In the illustrated exemplary embodiment, the second retaining mechanism includes a pair of alignment tabs about opposite lateral sides of the second locking mechanism directly engaging a corresponding pair of indentations about opposite lateral sides of the second locking mechanism.

As best shown in FIG. 1C, the first central cavity 112 of the first retaining mechanism 108 and the second central cavity 148 of the second retaining mechanism 124 are substantially aligned with a central axis "A"

A process for attaching the handle extension 150 to the second retaining housing 146 of the second retaining mechanism 124 at the proximal end 104 of the handle 102 is as follows. First, the user depresses the button end 174 of the second locking mechanism 160 that projects outwardly from the second retaining housing 146 (FIG. 4B) until the lip 168 no longer partially occludes the second central cavity 148 and the through hole 166 of the second locking mechanism is in substantial alignment with the second central cavity. The user then inserts a male connector 180 (FIG. 2C) of the handle extension 150 through the second central cavity 148 and the through hole 166 and releases the button end 174 of the second locking mechanism 160. The biasing member(s) 162 then urge the lip 168 of the second locking mechanism to engage a reduced diameter neck 182 adjacent the male connector of the handle extension and lock the handle extension to the second retaining mechanism 124.

As the lip 168 moves from the occluding first position to the non-occluding second position and back again, the indentation(s) 176 of the second locking mechanism 160 move relative to the alignment tab(s) 152. However, the opposite ends of the indentation(s) serve as stops to control the range of movement of the second locking mechanism 160 relative to the second retaining housing 146.

In order to remove either the surgical tool 114 or the handle extension 150 from the handle assembly 100, the user depresses the button ends 138, 174 of the first and second locking mechanisms 116, 160 until the lips 132, 168 no longer engage the reduced diameter necks 144, 182 of the surgical tool and the handle extension whereby the surgical tool and the handle extension may be withdrawn from the handle assembly.

In accordance with the exemplary embodiments, there is provided a universal handle assembly for a surgical tool to which a surgical tool and a handle extension may be easily attached and detached. Further, although not limited thereto, the handle assembly according to the subject disclosure finds beneficial use with implant extraction surgical tools.

It will be appreciated by those skilled in the art that changes could be made to the exemplary embodiments described above without departing from the broad 1s inventive concept thereof. It is to be understood, therefore, that this disclosure is not limited to the particular embodiments disclosed, but it is intended to cover modifications within the spirit and scope of the subject disclosure as defined by the appended claims.

I claim:
1. A handle assembly for a surgical tool comprising:
   a handle having a distal end; and
   a first retaining mechanism attached to the distal end of the handle, the first retaining mechanism including:
      a first retaining housing having a first central cavity for receiving a surgical tool,
      a first locking mechanism moveable between first and second positions relative to the housing, the first locking mechanism including a through hole for receiving the surgical tool, and
      a first alignment tab and a second alignment tab separate from and disposed about opposite lateral sides of the through hole of the first locking mechanism that limits movement of the first locking mechanism relative thereto.

2. The handle assembly of claim 1, wherein the first and second alignment tabs directly engage indentations about opposite lateral sides of the first locking mechanism.

3. The handle assembly of claim 1, wherein the first retaining housing includes a first bore and a second bore adjacent the first central cavity to receive the first and second alignment tabs of the first retaining mechanism.

4. The handle assembly of claim 1, wherein the first retaining mechanism further includes a first biasing member that biases the first locking mechanism towards the first position.

5. The handle assembly of claim 4, wherein the first biasing member directly engages the first locking mechanism.

6. The handle assembly of claim 1, wherein the first locking mechanism includes a lip that partially occludes the first central cavity when in the first position.

7. The handle assembly of claim 1, wherein the through hole of the first locking mechanism is larger than the first central cavity.

8. The handle assembly of claim 1, further comprising a second retaining mechanism attached to a proximal end of the handle, the second retaining mechanism including:
- a second retaining housing having a second central cavity for receiving a handle extension; and
- a second locking mechanism moveable between first and second positions relative to the second retaining housing, the second locking mechanism having a through hole for receiving the handle extension.

9. The handle assembly of claim 8, wherein the second retaining housing includes a plurality of fillets about its perimeter.

10. The handle assembly of claim 9, wherein the plurality of fillets circumscribes the second central cavity.

11. The handle assembly of claim 8, wherein the second retaining mechanism further includes a third alignment tab about a lateral side of the second locking mechanism that limits movement of the second locking mechanism.

12. The handle assembly of claim 11, wherein the third alignment tab directly engages an indentation about a lateral side of the second locking mechanism.

13. The handle assembly of claim 8, wherein the second retaining housing includes a bore adjacent the second central cavity to receive a third alignment tab of the second retaining mechanism.

14. The handle assembly of claim 8, wherein the second retaining mechanism further includes a second biasing member that biases the second locking mechanism towards the first position.

15. The handle assembly of claim 14, wherein the second biasing member directly engages the second locking mechanism.

16. The handle assembly of claim 8, wherein the second locking mechanism includes a lip that partially occludes the second central cavity from receiving the handle extension.

* * * * *